United States Patent
Onizawa et al.

(10) Patent No.: US 9,470,608 B2
(45) Date of Patent: Oct. 18, 2016

(54) SAMPLE PROCESSING SYSTEM

(75) Inventors: Kuniaki Onizawa, Hitachinaka (JP);
Hiroshi Ohga, Hitachiomiya (JP);
Tatsuya Fukugaki, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 270 days.

(21) Appl. No.: 13/825,982

(22) PCT Filed: Sep. 30, 2011

(86) PCT No.: PCT/JP2011/072538
§ 371 (c)(1),
(2), (4) Date: Apr. 27, 2013

(87) PCT Pub. No.: WO2012/046648
PCT Pub. Date: Apr. 12, 2012

(65) Prior Publication Data
US 2013/0202486 A1     Aug. 8, 2013

(30) Foreign Application Priority Data

Oct. 4, 2010 (JP) .................. 2010-225095

(51) Int. Cl.
*G01N 1/18*     (2006.01)
*G01N 35/00*     (2006.01)
(52) U.S. Cl.
CPC .......... *G01N 1/18* (2013.01); *G01N 35/00732* (2013.01); *G01N 2035/00861* (2013.01)
(58) Field of Classification Search
CPC ............. G01N 35/00732; G01N 1/18; G01N 2035/00861
USPC .................................................. 422/63-65
See application file for complete search history.

(56) References Cited

U.S. PATENT DOCUMENTS

| 5,814,276 A * | 9/1998 | Riggs .............................. 422/65 |
| 6,274,092 B1 * | 8/2001 | Itoh ........................... B01L 9/06 206/443 |

(Continued)

FOREIGN PATENT DOCUMENTS

| JP | 1-287464 A | 11/1989 |
| JP | 7-26767 U | 5/1995 |

(Continued)

OTHER PUBLICATIONS

English translation of International Preliminary Report on Patentability for International Patent Application No. PCT/JP2011/072538, transmitted May 16, 2013.

*Primary Examiner* — Jill Warden
*Assistant Examiner* — Julie Tavares
(74) *Attorney, Agent, or Firm* — Miles & Stockbridge P.C.

(57) ABSTRACT

This invention provides a sample processing system in which only one sample container is rested in one holder, the system being contemplated to prevent a mix-up of samples from occurring.
A barcode labeler module 13 includes an identifier-reading device R1 that reads an identifier of a holder holding a primary-sample container, a printer 13B that prints a label based on information from a control PC unit 21 as well as on the identifier of the primary-sample container holder that has been read by the identifier-reading device R1, and affixes the label to a secondary-sample container, and a second identifier-reading device R2 that reads an identifier of the holder having the secondary-sample container mounted therein. A aliquoter module 14 includes an identifier-reading device R3 that reads the identifier of the holder conveyed from the barcode labeler module 13 and having the primary-sample container mounted therein, an identifier-reading device R4 that reads the identifier of the holder having the secondary-sample container mounted therein, and a aliquoter unit 14A that dispenses a sample from the primary-sample container into the secondary-sample container.

7 Claims, 5 Drawing Sheets

(56) References Cited

U.S. PATENT DOCUMENTS

2005/0002828 A1* 1/2005 Gunji .............................. 422/99
2005/0013736 A1* 1/2005 McKeever ...................... 422/63

FOREIGN PATENT DOCUMENTS

| JP | 9-236608 A | 9/1997 |
| JP | 9-304399 A | 11/1997 |
| JP | 11-304814 A | 11/1999 |

* cited by examiner

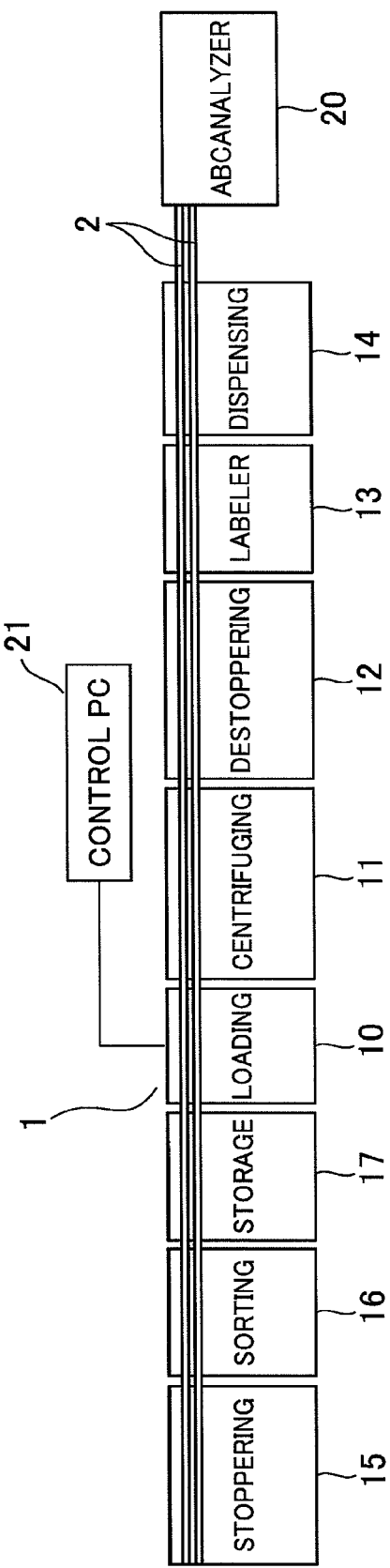
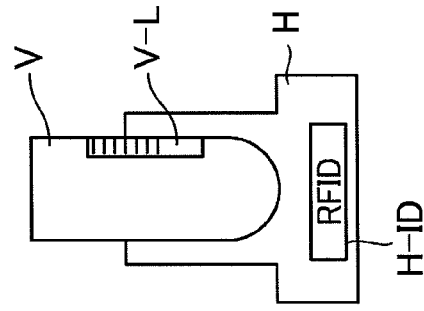

SAMPLE PROCESSING SYSTEM

TECHNICAL FIELD

The present invention relates generally to a sample processing system including an automated analytical system for analyzing blood, urine, and other samples, and a sample-preprocessing system for preprocessing these samples. More particularly, the invention relates to a sample processing system in which a plurality of preprocessing units, analyzing units, and the like are interconnected via conveyance lines.

BACKGROUND ART

Sample processing systems for automatically analyzing blood, urine, and other biological samples can be classified into two types. One is sample-preprocessing systems that each perform centrifugal separation, aliquot, labeling, and other processes, upon the blood, urine, and other samples that have been taken for tests. The other is automated analytical systems that each analyze the samples that have been processed by a sample-preprocessing system. Since these processes and analyses are diverse, a sample processing system is used in which each process is performed with an independent processing (analyzing) unit, and in which the processing (analyzing) units are interconnected via sample conveyance lines that convey the samples between the units.

Such a sample processing system performs a process of aliquot an indicated amount of blood sample, called a primary sample, from a blood-sampling tube into other containers (secondary-sample containers). In recent years, diversification of test items and reduction in test reporting time are demanded, and thus it is necessary for the system to quickly respond to aliquot the sample into a plurality of secondary-sample containers for respective test items. In addition, more efficient processing is required since a device error results in large quantities of unprocessed samples. Furthermore, the recognition of a primary sample and a secondary sample is gaining importance from a perspective of mix-up of samples.

The techniques described in Patent Documents 1 and 2, for example, are known as techniques for solving the above-mentioned problems.

PRIOR ART LITERATURE

Patent Documents

Patent Document 1: JP-1989-287464-A
Patent Document 2: JP-1999-304814-A

SUMMARY OF THE INVENTION

Problems to be Solved by the Invention

Typically, sample processing in conventional systems is executed on a rack-by-rack basis with five sample containers rested in one rack, but a mix-up of samples tends to be significantly influential in the conventional systems. The present inventors have therefore studied a system in which only one sample container is rested in one holder. It is however important to prevent samples from being mixed up, even in such a system.

An object of the present invention is to provide a sample processing system in which only one sample container is rested in one holder, the system being intended to prevent a mix-up of samples.

Means for Solving the Problems (1) In order to attain the above object, an aspect of the present invention is a sample processing system including: a conveyance line that conveys a holder between a labeling unit and a aliquoter unit; and a control unit that controls the labeling unit and the aliquoter unit; wherein: one primary-sample container or secondary-sample container is held in one holder; the labeling unit includes a first identifier-reading device that reads an identifier of the holder holding a primary-sample container conveyed by the conveyance line, a printer that prints a label based on information from the control unit as well as on the identifier, read by the first identifier-reading device, of the holder holding the primary-sample container, and affixes the label to a secondary-sample container, a mounting mechanism that mounts the labeled secondary-sample container in a holder, and a second identifier-reading device that reads an identifier of the holder having the secondary-sample container mounted therein; and the aliquoter unit includes a third identifier-reading device that reads the identifier of the holder conveyed from the labeling unit by the conveyance line and having the primary-sample container mounted therein, a fourth identifier-reading device that reads the identifier of the holder conveyed from the labeling unit by the conveyance line and having the secondary-sample container mounted therein, and a dispenser that dispenses a sample from the primary-sample container conveyed from the labeling unit by the conveyance line into the secondary-sample container conveyed from the labeling unit by the conveyance line.

The above system configuration prevents a mix-up of samples in the system constructed so that one primary-sample container or secondary-sample container only is held in one holder.

(2) In item (1) enumerated above, preferably, the control unit includes a collator adapted to check for matching between the identifier, read by the third identifier-reading device, of the holder holding the primary-sample container, and the identifier, read by the fourth identifier-reading device, of the holder holding the secondary-sample container. If a result of the identifier check by the collator indicates that the identifiers match, the control unit controls the dispenser to conduct aliquot. If the check result indicates a mismatch, aliquoter is not conducted, in which case, the holders are unloaded and the identifiers and other information relating to the holders are displayed at a control PC unit so that the information can be confirmed.

(3) In item (2) enumerated above, the third and fourth identifier-reading devices are preferably each disposed immediately before the aliquoter unit with respect to a direction in which the holder is conveyed by the conveyance line.

(4) In item (3) enumerated above, preferably, the aliquoter unit also includes an information-writing device adapted to write information onto the holder holding the sample container into which the dispenser has dispensed the sample, and the control unit includes an information output section that outputs the amount of dispensed sample and information on interim stopovers, to the information-writing device.

(5) In item (1), preferably, the aliquoter unit further includes a plurality of secondary lines as the conveyance line, the secondary lines being adapted for parallel conveyance of holders each having a secondary-sample container mounted therein, and a fifth identifier-reading device that reads an identifier of the holder conveyed from the labeling unit by the conveyance line and having the secondary-sample container mounted therein. Furthermore, the aliquoter unit is configured to dispense a sample from the primary-sample container into each of the secondary-sample containers conveyed by the secondary lines. The printer prints labels based on the identifier, read by the first identifier-reading device, of the holder holding the primary-sample container, and affixes the labels to the secondary-sample containers. The control unit smoothes the conveyance of the holders holding the secondary-sample containers, with respect to the secondary lines, the control unit including a collator adapted to check for matching between the identifier, read by the third identifier-reading device, of the holder having the primary-sample container mounted therein, and the identifiers, read by the fourth and fifth identifier-reading devices, of the holders having the secondary-sample containers mounted therein. The control unit also controls the dispenser to conduct aliquot if identifier check results by the collator indicate that the identifiers match.

Effects of the Invention

In accordance with the present invention, the system in which one sample container is rested in one holder prevents a mix-up of samples.

BRIEF DESCRIPTION OF THE DRAWINGS

FIG. 1 is a block diagram showing an overall configuration of a sample processing system according to an embodiment of the present invention;

FIG. 2 is a front view that shows constituent elements of a holder and sample container used in the sample processing system according to the embodiment of the present invention;

MODE FOR CARRYING OUT THE INVENTION

Figure 3:
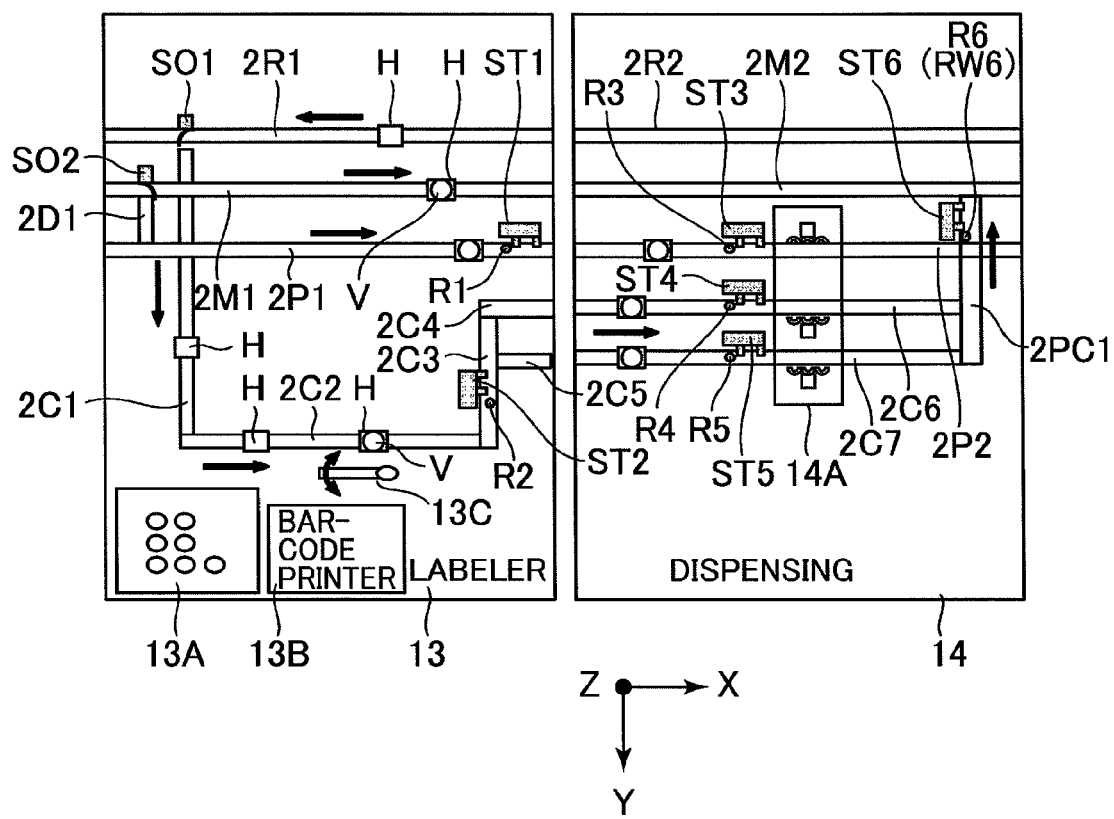
FIG. 3 is a plan view showing a detailed configuration of a barcode labeler module and aliquoter module of a biological-sample preprocessing system included in the sample processing system according to the embodiment of the present invention.

Hereunder, a configuration and operation of a sample processing system according to an embodiment of the present invention will be described using FIGS. 1 to 6.

An overall configuration of the sample processing system according to the present embodiment is first described below using FIG. 1.

FIG. 1 is a block diagram showing the overall configuration of the sample processing system according to the embodiment of the present invention.

The sample processing system according to the present embodiment includes a preprocessing system that preprocesses biological samples (blood samples) that have been taken from patients, and an automated analyzing apparatus that analyzes the preprocessed biological samples.

The preprocessing system 1 that preprocesses the biological samples includes a plurality of modules as basic elements, which are a input buffer module 10, a Automatic centrifuge module 11, a destopper module 12, a (typically, bar-code) barcode labeler module 13, a aliquoter module 14, a restopper module 15, a sorter module 16, and a output buffer module 17. The control PC unit 21 controls the entire preprocessing system 1.

The automated analyzing apparatus 20 analyzes composition of each biological sample which has preprocessed by the preprocessing system 1. The automated analyzing apparatus 20 is typically composed of a plurality of analyzers including a biochemical analyzer, an immunoassay analyzer, and so on.

Inside the preprocessing system 1 and between the preprocessing system 1 and the automated analyzing apparatus 20, samples (sample containers) are conveyed using conveyance lines 2.

The input buffer module 10 loads a sample into the biological-sample preprocessing system. The Automatic centrifuge module 11 centrifuges the loaded sample. The destopper module 12 opens a stopper of the centrifuged sample. The aliquoter module 14 divides the centrifuged sample (primary sample) into smaller amounts of samples (secondary samples) for analysis in the automated analyzing apparatus 20 or the like. That is to say, the primary sample stored within the primary-sample container conveyed by one of the conveyance lines 2 is dispensed into a plurality of secondary-sample containers. The barcode labeler module 13 affixes bar-code labels to the secondary-sample containers into which the primary sample has been dispensed in smaller amounts.

The restopper module 15 closes the stopper of each sample container. The output buffer module 17 stores each stoppered sample container and primary-sample container. The sorter module 16 classifies the secondary-sample containers.

Constituent elements of a holder and sample container used in the sample processing system according to the embodiment of the present invention are next described below using FIG. 2.

FIG. 2 is a front view that shows the constituent elements of the holder and sample container used in the sample processing system according to the embodiment of the present invention.

The sample container V is held in the holder H. One holder H holds one sample container V only. A biological sample is stored within the sample container V.

A label V-L is affixed to the sample container V. The sample container V has a shape like a test tube. In other words, the sample container V has a semi-spherically based/bottomed cylindrical shape.

Primary-sample containers and secondary-sample containers exist as sample containers V. Primary-sample containers are brought in from hospitals, clinics, and the like requiring laboratory tests of biological samples. Primary-sample containers come in several kinds of geometries. Although primary-sample containers have the shape of a test tube, some differ in diameter and some differ in height. The holder H has or may have, for example, a spring-loaded clamping mechanism, which allows the holder to hold any one of a plurality of primary-sample containers different in shape. Labels V-L for primary-sample containers are affixed thereto in the hospital, the clinic, or the like beforehand. A bar code is printed on the label V-L of each primary-sample container beforehand. The bar code contains an ID of the sample (i.e., information such as a name of the patient who supplied the biological sample) and test item information. An external reading device can read the bar-code information in a non-contact condition.

Secondary-sample containers are supplied from the barcode labeler module 13 shown in FIG. 1, and all are of the same shape. Labels V-L for secondary-sample containers are affixed thereto by the barcode labeler module 13 shown in FIG. 1. A bar code is printed on the label V-L of each secondary-sample container by the barcode labeler module 13. The bar code contains unique information (e.g., a serial number and other information) identifying the secondary-sample container, and an ID of the primary sample. The external reading device can read the bar-code information in a non-contact condition.

The holder H has an RF-ID section therein. The RF-ID section has a storage portion, and the storage portion includes an identifier that identifies the holder H. The external reading device can use a radio wave to read out in non-contact form the identifier stored within the storage portion of the RF-ID section. The external reading device can also write information into the storage portion of the RF-ID section using a radio wave.

The control PC unit 21 includes an information management section. In the information management section, the patient name and other information retained in the bar code of the primary-sample container, the test item information, and the identifier information retained in the RF-ID section of the holder H for holding the primary-sample container are input in associated form beforehand. The barcode labeler module 13 associates the unique information identifying the secondary-sample container with the identifier of the holder H holding the secondary-sample container, and transmits the two kinds of associated information to the information management section of the control PC unit 21. Thus, when the aliquoter module 14 shown in FIG. 1 dispenses part of the primary sample from the primary-sample container into the secondary-sample container, the information management section can associate the identifier of the holder H holding the primary-sample container with that of the holder H holding the secondary-sample container, and manage and display the identifiers. The display of the managed information also allows confirmation of the information.

Next, a detailed configuration of the barcode labeler module 13 and aliquoter module 14 of the biological-sample preprocessing system included in the sample processing system according to the present embodiment is described below using FIG. 3. In addition, a configuration and operation of the control PC unit 21 used in the sample processing system according to the present embodiment are described below using FIG. 4.

Figure 4:
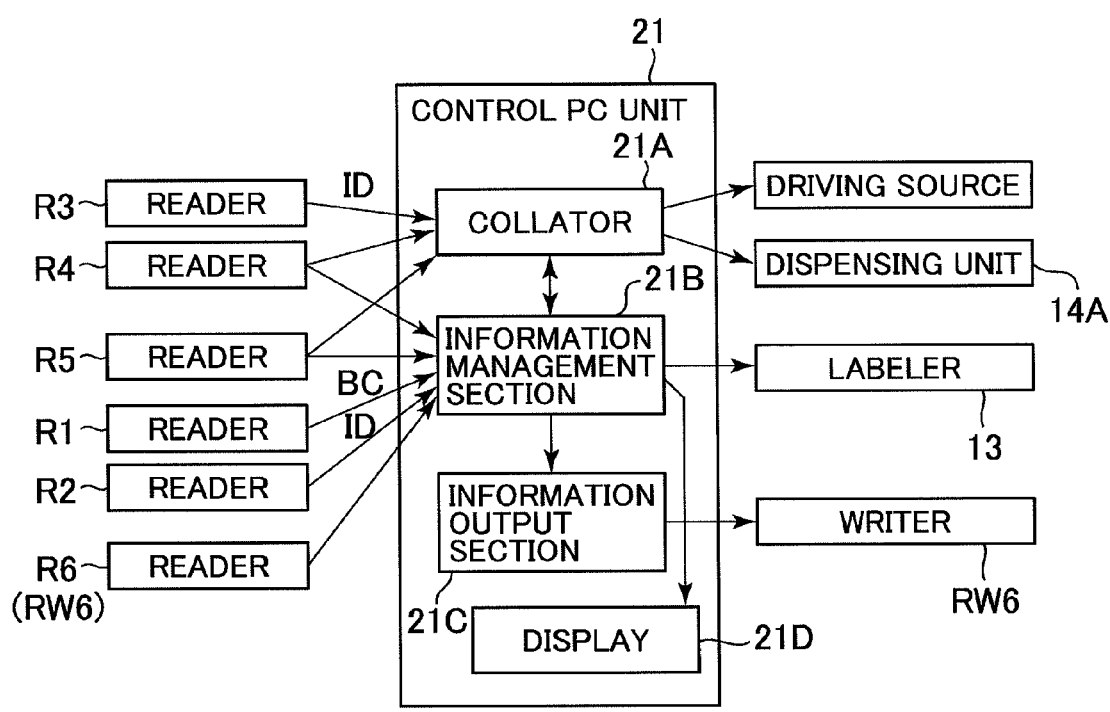
FIG. 4 is a block diagram showing a configuration of a control PC unit used in the sample processing system according to the embodiment of the present invention.

FIG. 3 is a plan view showing the detailed configuration of the barcode labeler module and aliquoter module of the biological-sample preprocessing system included in the sample processing system according to the embodiment of the present invention. FIG. 4 is a block diagram showing the configuration of the control PC unit used in the sample processing system according to the present embodiment.

The barcode labeler module 13 includes a return line 2R1, a main line 2M1, a primary line 2P1, a branch line 2D1, and secondary lines 2C1, 2C2, 2C3, 2C4, 2C5, as the conveyance lines 2 shown in FIG. 1. Each conveyance line 2 conveys a holder H in a direction of an arrow. Each conveyance line 2 is driven by an independent driving source. Adjacent conveyance lines 2 can each convey the holder H continuously. For example, the holder H that has been conveyed in the direction of the arrow by the secondary conveyance line 2C1 can be next conveyed by the secondary conveyance line 2C2.

The main line 2M1 and the primary line 2P1 are provided at the same height position. The return line 2R1 is provided at a lower position than the main line 2M1 and the primary line 2P1. In contrast to this, the secondary line 2C1 is constructed with a flat path and an upward sloped path in combination so that the holder H conveyed by the return line 2R1 can pass under the main line 2M1 and the primary line 2P1.

The aliquoter module 14 includes a return line 2R2, a main line 2M2, a primary line 2P2, secondary lines 2C6, 2C7, and a primary/secondary conveyance line 2PC1, as the conveyance lines 2 shown in FIG. 1. Each conveyance line 2 conveys a holder H in a direction of an arrow. Each conveyance line 2 is driven by an independent driving source. Adjacent conveyance lines 2 can each convey the holder H continuously.

The adjacent conveyance lines 2 in the barcode labeler module 13 and aliquoter module 14 can continuously convey the holder H. For example, the holder H that has been conveyed in the direction of the arrow by the return line 2R2 can be next conveyed by the return line 2R1.

The return lines 2R1, 2R2 usually convey only holders H not holding a sample container. Holders H not holding the sample container that has been conveyed in the direction of the arrow by the return line 2R1 are appropriately sorted by a sorting mechanism SO1 and directed towards the secondary line 2C1. In addition, if a holder H holding a sample container which requires a retest is conveyed by the return line 2R1, then the holder H is caused, by the sorting mechanism SO1, to move straight ahead as it is along the return line 2R1, and conveyed to the input buffer module 10 shown in FIG. 1.

The holder H holding the primary-sample container in which the primary sample having undergone the previous step is accommodated is conveyed from the direction of the input buffer module 10 shown in FIG. 1, to the primary line 2P1. In addition, a holder H holding a primary-sample container in which an urgent sample is accommodated is conveyed to the main line 2M1. The urgent sample, if does not require aliquot by the aliquoter module 14, is appropriately sorted by the sorting mechanism SO1 so as to move straight ahead as it is, and conveyed by the main line 2M1 or 2M2 to the automated analyzing apparatus 20 shown in FIG. 1. If aliquot is required, the holder H holding the primary-sample container in which the urgent sample is accommodated is appropriately sorted by the sorting mechanism SO2 so as to change the direction thereof to the primary line 2P1 through the branch line 2D1, and conveyed to 2P1.

A stopper ST1 and an identifier-reading device R1 are provided midway on the primary line 2P1. The stopper ST1 halts the holder H that has been conveyed by the primary line 2P1. The identifier-reading device R1 reads the identifier of the holder H. The identifier of the holder H that has been read is sent to the information management section 21B of the control PC unit 21. The information management section 21B of the control PC unit 21 acquires, from the identifier of the holder H, the information relating to the primary sample in the container mounted in the holder H. The information management section 21B determines a necessary number of secondary samples from the information relating to the primary sample, and outputs the unique information contained in the bar code of each secondary sample to the bar-code printer 13B of the barcode labeler module 13. That is to say, the barcode labeler module 13 creates two secondary-sample containers and the aliquoter module 14 for a step which immediately follows labeling creates two secondary samples by aliquot the primary sample held in the primary-sample container.

Upon completion of holder identifier reading by the identifier-reading device R1, the halt of the holder H by the stopper ST1 is released and the holder H is conveyed from the primary line 2P1 to the primary line 2P2 of the aliquoter module 14.

A holder H not holding the sample container that has been conveyed by the secondary line 2C1 is conveyed by the secondary line 2C2, and in the course of the conveyance, a secondary-sample container V-C is mounted in the holder H by a secondary-sample mounting mechanism 13C.

In addition to the secondary-sample mounting mechanism 13C, the barcode labeler module 13 includes a secondary-sample container storage unit 13A and the bar-code printer 13B. A large number of empty secondary-sample containers V-C are accommodated in the secondary-sample container storage unit 13A. The bar-code printer 13B prints a bar code onto a label, and affixes the printed label to one of the secondary-sample containers that has been taken out from the secondary-sample container storage unit 13A.

A stopper ST2 and an identifier-reading device R2 are provided midway on the secondary line 2C2. The stopper ST2 halts a holder H that has been conveyed by the secondary line 2C2.

The secondary-sample mounting mechanism 13C mounts the labeled secondary-sample container V-C in the holder H which has conveyed by the secondary line 2C2. The identifier-reading device R2 reads the identifier of the holder H. The identifier of the holder H that has been read is sent to the information management section 21B of the control PC unit 21. The information management section 21B of the control PC unit 21 associates and manages the identifier of the holder H and the information contained in the label of the secondary-sample container V-C mounted in the holder H.

Upon completion of holder identifier reading by the identifier-reading device R2, the halt of the holder H by the stopper ST2 is released and the holder H is conveyed to secondary line 2C3.

The above sequence is repeated to create a plurality of secondary samples in conformity with the information assigned to the primary sample.

The holder H with the secondary-sample container V-C mounted therein is conveyed from the secondary line 2C3 to either of the secondary lines 2C4, 2C5, depending on whether sample undergoes independent processing for each analytical item, test item, or the like. At this time, the secondary samples created by the barcode labeler module 13 are conveyed alternately to the secondary lines 2C4 and 2C5, thereby aliquot is smoothed. In other words, the number of secondary samples to be created differs according to the number of test items executed for the primary sample. Accordingly, the secondary samples created by the barcode labeler module 13 are conveyed alternately to the secondary lines 2C4 and 2C5 so that the number of secondary samples conveyed by the secondary lines 2C4 and 2C5 is balanced between both of the secondary lines.

Next, a configuration and operation of the aliquoter module 14 are described below.

A holder H with a primary-sample container V-P mounted therein is conveyed by the primary line 2P2 and then halted by a stopper ST3 in the aliquoter module 14, and the identifier of the holder H is read by an identifier-reading device R3. The identifier that has been read is sent to the control PC unit 21. A collator 21A in the control PC unit 21 obtains from the information management section 21B the information assigned to the primary sample corresponding to the identifier of the holder H that was read, and then obtains aliquot information.

In the meantime, a holder H that has been conveyed by the secondary line 2C6 or 2C7 is halted by a stopper ST4 or ST5 and then the identifier of the holder H is read by an identifier-reading device R4 or R5. The identifier that has been read is sent to the control PC unit 21. The collator 21A in the control PC unit 21 obtains from the information management section 21B the information assigned to the secondary sample corresponding to the identifier of the holder that was read. The collator 21A cross-checks the information assigned to the primary sample, and the information assigned to the secondary sample. If check results indicate matching, the holder H holding the primary-sample container V-P, and the holder H holding the secondary-sample container V-C are conveyed to a position of a aliquoter unit 14A by the primary line 2P2 and the secondary line 2C6, 2C7, respectively. The aliquoter unit 14A includes a aliquot nozzle. The aliquot nozzle is configured to be actuated in directions of X-, Y-, and Z-axes by an XYZ mechanism. The aliquot nozzle descends in the direction of the Z-axis from a position above the primary-sample container, then aspirates a predetermined amount of primary sample from the primary-sample container, and ascends in the direction of the Z-axis. Next, the aliquot nozzle moves in the direction of the Y-axis, then after stopping above the secondary-sample container, descends in the direction of the Z-axis once again, and discharges the primary sample into the secondary-sample container. If a plurality of secondary-sample containers are present, the above sequence is repeated for each of the secondary-sample containers. Thus, the primary sample is dispensed in smaller amounts into the secondary-sample containers.

After aliquot, the holder H holding the primary-sample container is conveyed from the primary line 2P2 to an integrated line 2PC1. Similarly, the holders H holding the secondary-sample container into which the primary sample has been dispensed are each conveyed from the secondary lines 2C6, 2C7 to the primary/secondary conveyance line 2PC1. Each holder H that has been conveyed to the primary/secondary conveyance line 2PC1 comes to a halt at a stopper ST6 and after the identifier of the holder H has been read by an identifier-reading device R6, the identifier information is sent to the control PC unit 21 and managed. The information can be confirmed via a display 21D.

The identifier-reading device R6 can be replaced by a read/write device RW6, which allows not only the above information to be read, but also the amount of aliquot, information on interim stopovers, and other information to be written using the information output section 21C. Thus, these kinds of information can be assigned to identifiers and managed by means of the identifiers.

Next, operation of the collator 21A in the sample processing system according to the present embodiment is described below using FIG. 5.

Figure 5:
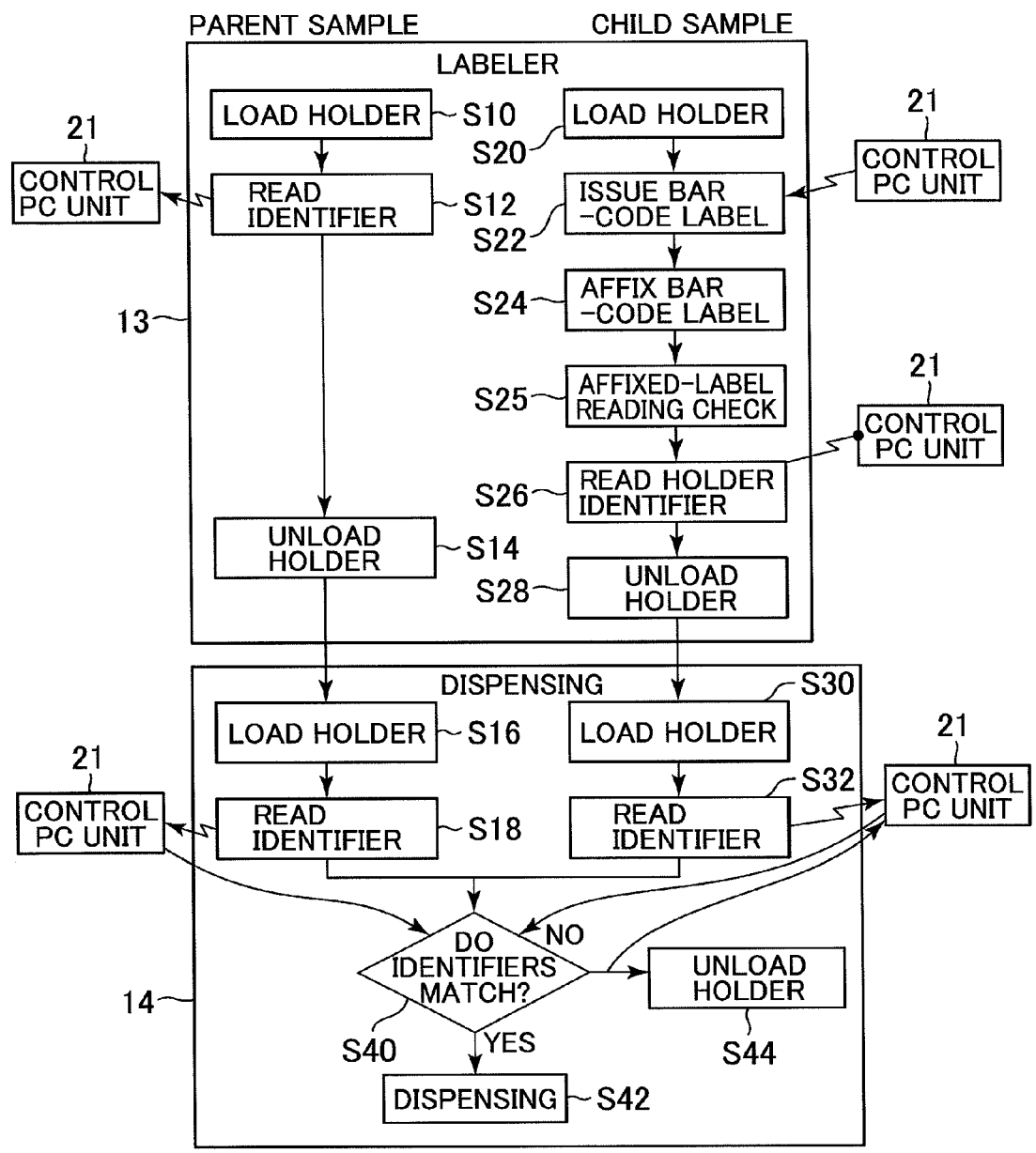
FIG. 5 is a flowchart showing a flow of collator operation in the sample processing system according to the embodiment of the present invention.

FIG. 5 is a flowchart showing a flow of collator operation in the sample processing system according to the embodiment of the present invention.

In the barcode labeler module 13, after the holder with the primary-sample container mounted therein has been carried in (step S10), the identifier-reading device R1 reads the identifier of the holder H (step S12) and transmits the identifier information to the control PC unit 21.

Additionally, after a holder for a secondary-sample container has been carried into the barcode labeler 13 (step S20), the information management section of the control PC unit 21 sends to the barcode labeler module 13 the issuance information relating to the bar-code label for secondary samples, based on the identifier information relating to the holder in which the primary-sample container is mounted. The bar-code printer 13B then issues the secondary-sample bar-code label based on the issuance information (step S22), attaches the bar-code label to a sample container (step S24), and mounts the sample container tube in the holder. The identifier-reading device R2 reads the identifier of the holder (step S26) and transmits the identifier information to the control PC unit 21.

Thereafter, the holder with the primary-sample container mounted therein, and the holder holding the secondary-sample container are unloaded into the aliquoter module 14 separately (steps S14, S28).

The above two holders that have been unloaded from the barcode labeler module 13 are carried into the aliquoter module 14 separately (steps S16, S30). The identifiers of the two holders which have been carried in from the barcode labeler module are read (steps S18, S32), the control PC unit 21 checks for matching in primary relationship (step S40), and if the holders are found to match in primary relationship, the primary sample is dispensed from the primary-sample container into the secondary-sample container (step S42). The holders, if found not to match, are unloaded from the aliquoter module 14 (step S44) and aliquot is not executed. In addition, a bar-code labeling/identifier reading check (step S25) can be conducted between the attachment of the bar-code label to the test tube (step S24) and the reading of the holder identifier (step S26). In this case, aliquot is also skipped if an error occurs during the execution of the bar-code labeling/identifier reading check (step S25). The identifier mismatch information and bar-code labeling/identifier reading check error information described above can be confirmed via the display 21D of the control PC unit 21.

Next, an operational variant of the collator 21A in the sample processing system according to the present embodiment is described below using FIG. 6.

Figure 6:
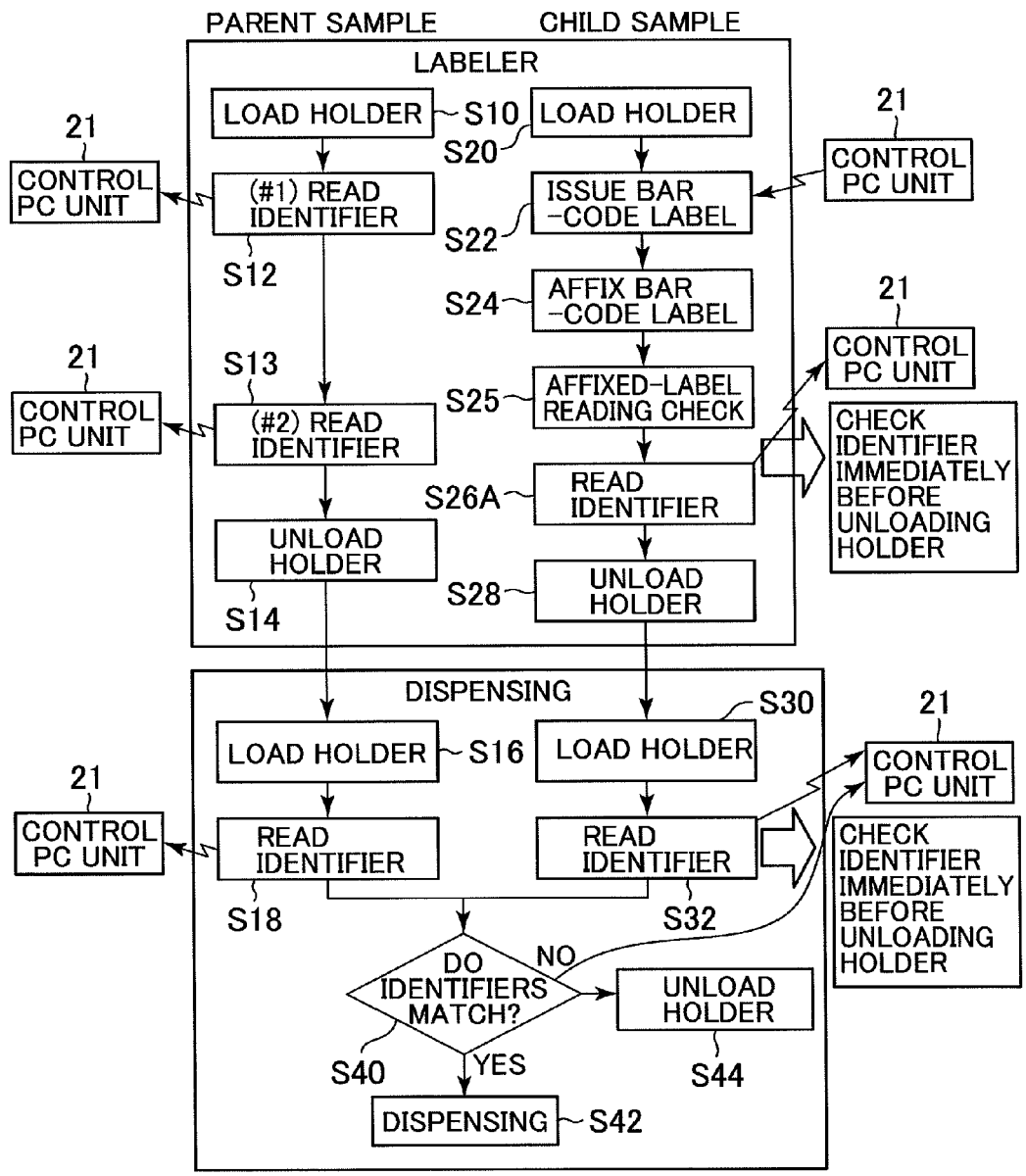
FIG. 6 is a flowchart showing an operational variant of the collator in the sample processing system according to the embodiment of the present invention.

FIG. 6 is a flowchart showing the operational variant of the collator in the sample processing system according to the embodiment of the present invention.

In the present variant, in addition to the operational sequence shown in FIG. 5, the identifiers of the primary-sample container and secondary-sample container holders are read (steps S13, S26A) immediately before the two holders are unloaded from the barcode labeler module 13, and at the same time, the holders are unloaded into the aliquoter module 14.

In the aliquoter module 14, as described above, the identifiers of the primary-sample container and secondary-sample container holders are also read (steps S18, S32) immediately after holder loading into the barcode labeler module and the aliquoter module, the holders are checked against each other, and aliquot is conducted.

In this way, the identifiers are read immediately before holder unloading and immediately after holder loading (carrying-in), so that a recognition error between the primary-sample container and the secondary-sample container is prevented from occurring. Hence, the primary sample and the secondary sample undergo highly efficient processing and the aliquot information checks are strengthened.

Forming the barcode labeler module 13 and the aliquoter module 14 into an integrated structure for omission of holder unloading and loading between the modules also allows the identifiers to be correctly recognized and checked, even with the second and third identifier-reading devices alone, and thus a recognition error between the primary-sample container and the secondary-sample container to be prevented from occurring.

The sample processing system of the present embodiment that has the above configuration/construction and operates as described above has the following features and characteristics.

First, the barcode labeler module 13 includes: the first identifier-reading device R1 that reads the identifier of a holder holding a primary-sample container which has been conveyed by one of the conveyance lines; the printer 13B that prints a label based on information from the control PC unit 21 as well as on the identifier, of the primary-sample container holder, read by the first identifier-reading device, and affixes the label to a secondary-sample container; the mounting mechanism 13C that mounts the labeled secondary-sample container in a holder; and the second identifier-reading device R2 that reads the identifier of the holder having the secondary-sample container mounted therein.

In addition, the aliquoter module 14 includes: the third identifier-reading device R3 that reads the identifier of the holder conveyed from the barcode labeler module 13 by one of the conveyance lines and having the primary-sample container mounted therein; the fourth identifier-reading device R4 that reads the identifier of the holder conveyed from the barcode labeler module 13 by one of the conveyance lines and having the secondary-sample container mounted therein; and the aliquoter unit 14A that dispenses a sample from the primary-sample container conveyed from the barcode labeler module 13 by one of the conveyance lines into the secondary-sample container conveyed from the barcode labeler module 13 by one of the conveyance lines.

The above system configuration prevents a mix-up of samples in the system so constructed that one primary-sample container or secondary-sample container is held in one holder.

Second, the control PC unit 21 includes the collator 21A that checks for matching between the identifier, read by the third identifier-reading device R3, of the holder holding the primary-sample container, and the identifier, read by the fourth identifier-reading device R4, of the holder holding the secondary-sample container. If a result of the identifier check by the collator 21A indicates that the identifiers match, the control PC unit 21 controls the aliquoter module 14 to conduct aliquot. If the check result indicates a mismatch, aliquot is not conducted, in which case, the identifiers of the holders and other information relating to the holders are displayed on the display 21D of the control PC unit 21 so that the information can be confirmed.

This prevents a mix-up of samples during aliquot.

Third, the third and fourth identifier-reading devices R3 and R4 are each disposed immediately before the aliquoter unit with respect to the direction in which the holder is conveyed by the conveyance line.

Here, if a device error occurs, the sample being processed or waiting for processing is likely to be conveyed in that unprocessed condition and require manual processing in a later step. In the present embodiment, however, since each holder is processed independently and the information to undergo processing is managed by the control PC unit, if the third and fourth identifier-reading devices R3 and R4 are made to read the identifiers once again, the information to undergo processing can be obtained from the control PC unit, so that no sample is conveyed in an unprocessed condition and thus so that manual processing loads in subsequent steps are reduced.

Fourth, the aliquoter unit 14A further includes the information read/write device RW6 that can write information onto the holder holding the sample container into which the dispenser has dispensed the sample. The control PC unit 21 includes the information output section 21C that outputs the amount of dispensed sample and information on interim stopovers, to the information read/write device RW6.

Thus, these kinds of information can be assigned to identifiers and managed by means of the identifiers.

Fifth, the aliquoter module 14 further includes, as the conveyance lines, the plurality of secondary lines 2C6, 2C7 adapted for parallel conveyance of holders each having a secondary-sample container mounted therein, and the fourth, fifth identifier-reading device R4, R5 that reads the identifier of the holder conveyed from the barcode labeler module 13 by one of the conveyance lines and having the secondary-sample container mounted therein. Furthermore, the aliquoter unit 14A is configured to dispense a sample from the primary-sample container into each of the secondary-sample containers conveyed by the secondary lines. The printer 13B prints labels based on the identifier, read by the first identifier-reading device R1, of the primary-sample container holder, and affixes the labels to the secondary-sample containers. The control PC unit 21 smoothes the conveyance of the holders holding the secondary-sample containers, with respect to the secondary lines. The control PC unit 21 additionally includes the collator 21A that checks for matching between the identifier, read by the third identifier-reading device R3, of the holder having the primary-sample container mounted therein, and the identifiers, read by the fourth and fifth identifier-reading devices R4 and R5, of the holders having the secondary-sample containers mounted therein. The control PC unit 21 also controls the aliquoter module 14 to conduct aliquot if results of the identifier checks by the collator 21A indicate that the identifiers match.

Sixth, forming the barcode labeler module 13 and the aliquoter module 14 into an integrated structure for omission of holder unloading and loading between the modules allows identifiers to be correctly recognized and checked since the second identifier-reading device R2 and the third identifier-reading devices R3 exist, and thus a sample recognition error during aliquot to be prevented from occurring.

These features and characteristics of the sample processing system allow it to respond to diversification of test items, and to execute rapid aliquot into a plurality of sample containers.

DESCRIPTION OF REFERENCE NUMBERS

1 . . . Preprocessing system
2 . . . Conveyance lines
2C . . . Secondary line
2P . . . Primary line
2M . . . Main line
2R . . . Return line
10 . . . Input buffer module
11 . . . Automatic centrifuge module
12 . . . Destopper module
13 . . . Barcode labeler module
13A . . . Secondary-sample container storage unit
13B . . . Bar-code printer
13C . . . Secondary-sample container mounting mechanism
14 . . . Aliquoter module
14A . . . Aliquoter unit
15 . . . Restopper module
16 . . . Sorter module
17 . . . Output buffer module
20 . . . Analyzing apparatus
21 . . . Control PC unit
ST . . . Stopper
R . . . Identifier-reading device

The invention claimed is:

1. A sample processing system comprising:
a labeling unit that affixes a label to a second container;
an aliquoter unit comprising a dispenser that dispenses a sample from a first container to the second container;
a first conveyance line that conveys a first holder, which holds the first container, from the labeling unit to the aliquoter unit;
a second conveyance line that conveys a second holder from the labeling unit to the aliquoter unit, the second holder being configured to hold the second container; and
a control unit that controls the labeling unit and the aliquoter unit,
wherein the labeling unit includes:
a first identifier-reading device for the first conveyance line that reads a first identifier of the first holder holding the first container conveyed by the first conveyance line,
a printer that is arranged along the second conveyance line, that prints the label based on the first identifier, provided by the control unit and read by the first identifier-reading device, of the first holder, and that affixes the label to the second container,
a mounting mechanism that is arranged along the second conveyance line and that mounts the labeled second container in the second holder, and
a second identifier-reading device that is arranged downstream of the mounting mechanism along the second conveyance line and that reads a second identifier of the second holder having the second container mounted therein,
wherein the aliquoter unit includes:
a third identifier-reading device for the first conveyance line that reads the first identifier of the first holder, which holds the first container, conveyed from the labeling unit by the first conveyance line, and
a fourth identifier-reading device for the second conveyance line that reads the second identifier of the second holder, which holds the second container, conveyed from the labeling unit by the second conveyance line,
wherein the dispenser is arranged downstream from the third and fourth identifier-reading devices and dispenses a sample from the first container conveyed from the labeling unit by the first conveyance line into the second container conveyed from the labeling unit by the second conveyance line,
wherein the control unit is configured to check for matching between the first identifier, read by the third identifier-reading device, of the first holder holding the first container, and the second identifier, read by the fourth identifier-reading device, of the second holder holding the second container, and
wherein, if said check indicates that the first and second identifiers match, the control unit is further configured to control the dispenser to dispense the sample from the first container into the second container.

2. The sample processing system according to claim 1, wherein:

the third and fourth identifier-reading devices are each disposed upstream of the dispenser.

3. The sample processing system according to claim 1, wherein:

the aliquoter unit further includes an information-writing device adapted to write information onto the second holder holding the second container into which the dispenser has dispensed the sample; and the control unit includes an information output section that outputs an amount of dispensed sample and information on interim stopovers, to the information-writing device.

4. The sample processing system according to claim 1, wherein:

the aliquoter unit further includes:

a third conveyance line that conveys another second holder, which holds another second container, each of the second and third conveyance lines being adapted for parallel conveyance of the second holders, and a fifth identifier-reading device for the third conveyance line that reads another second identifier of the another second holder having the another second container mounted therein;

the dispenser is configured to dispense a respective portion of the sample from the first container into each of the second containers conveyed by the second and third conveyance lines;

the printer prints respective labels based on the first identifier, read by the first identifier-reading device, of the first holder, and affixes the labels to the second containers;

the control unit is configured to manage conveyance of the second holders holding the second containers, between the second and third conveyance lines, the control unit is configured to check for matching between the first identifier, read by the third identifier-reading device, of the first holder having the first container mounted therein, and the second identifiers, read by the fourth and fifth identifier-reading devices, of the second holders having the second containers mounted therein, and the control unit is further configured to control the dispenser to dispense if said check indicates that the first and second identifiers match.

5. The sample processing system according to claim 1, wherein the control unit is configured to provide a notification if said check indicates that the first and second identifiers do not match.

6. The sample processing system according to claim 1, further comprising a return line that conveys the second holder without any second container to an input portion of the labeling unit.

7. The sample processing system according to claim 1, further comprising a main line that conveys the second holder holding the second container from the second conveyance line to an automatic analyzer apparatus for processing of the sample in the second container.

\* \* \* \* \*